(12) United States Patent
Viswanathan

(10) Patent No.: US 8,273,081 B2
(45) Date of Patent: Sep. 25, 2012

(54) IMPEDANCE-BASED CARDIAC THERAPY PLANNING METHOD WITH A REMOTE SURGICAL NAVIGATION SYSTEM

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1352 days.

(21) Appl. No.: 11/852,950

(22) Filed: Sep. 10, 2007

(65) Prior Publication Data

US 2008/0065061 A1 Mar. 13, 2008

Related U.S. Application Data

(60) Provisional application No. 60/843,529, filed on Sep. 8, 2006.

(51) Int. Cl.
*A61B 18/12* (2006.01)
(52) U.S. Cl. .......................................................... 606/32
(58) Field of Classification Search .............. 606/32–50; 128/898
See application file for complete search history.

(56) References Cited

U.S. PATENT DOCUMENTS

| | | | | |
|---|---|---|---|---|
| 5,297,549 A | * | 3/1994 | Beatty et al. | 600/374 |
| 5,409,000 A | * | 4/1995 | Imran | 600/374 |
| 5,654,864 A | | 8/1997 | Ritter et al. | |
| 5,931,818 A | | 8/1999 | Werp et al. | |
| 6,014,580 A | | 1/2000 | Blume et al. | |
| 6,015,414 A | | 1/2000 | Werp et al. | |
| 6,106,466 A | * | 8/2000 | Sheehan et al. | 600/443 |
| 6,128,174 A | | 10/2000 | Ritter et al. | |
| 6,148,823 A | | 11/2000 | Hastings | |
| 6,152,933 A | | 11/2000 | Werp et al. | |
| 6,157,853 A | | 12/2000 | Blume et al. | |
| 6,212,419 B1 | | 4/2001 | Blume et al. | |
| 6,241,671 B1 | | 6/2001 | Ritter et al. | |
| 6,292,678 B1 | | 9/2001 | Hall et al. | |
| 6,296,604 B1 | | 10/2001 | Garibaldi et al. | |
| 6,298,257 B1 | | 10/2001 | Hall et al. | |
| 6,304,768 B1 | | 10/2001 | Blume et al. | |
| 6,315,709 B1 | | 11/2001 | Garibaldi et al. | |
| 6,330,467 B1 | | 12/2001 | Creighton, IV et al. | |
| 6,352,363 B1 | | 3/2002 | Munger et al. | |
| 6,364,823 B1 | | 4/2002 | Garibaldi et al. | |
| 6,375,606 B1 | | 4/2002 | Garibaldi et al. | |
| 6,385,472 B1 | | 5/2002 | Hall et al. | |
| 6,401,723 B1 | | 6/2002 | Garibaldi et al. | |
| 6,428,551 B1 | | 8/2002 | Hall et al. | |
| 6,459,924 B1 | | 10/2002 | Creighton, IV et al. | |
| 6,475,223 B1 | | 11/2002 | Werp et al. | |
| 6,505,062 B1 | | 1/2003 | Ritter et al. | |
| 6,507,751 B2 | | 1/2003 | Blume et al. | |
| 6,522,909 B1 | | 2/2003 | Garibaldi et al. | |
| 6,524,303 B1 | | 2/2003 | Garibaldi | |
| 6,527,782 B2 | | 3/2003 | Hogg et al. | |
| 6,537,196 B1 | | 3/2003 | Creighton, IV et al. | |
| 6,542,766 B2 | | 4/2003 | Hall et al. | |
| 6,562,019 B1 | | 5/2003 | Sell | |

(Continued)

*Primary Examiner* — Michael Peffley
*Assistant Examiner* — Ronald Hupczey, Jr.
(74) *Attorney, Agent, or Firm* — Harness, Dickey & Pierce, P.L.C.

(57) ABSTRACT

A method is disclosed for planning the treatment of cardiac arrhythmias by RF ablation with a remote navigation system, including the identification of ablation lines around the pulmonary veins ostia—atrial junctions based on impedance measurements. When used by itself or in conjunction with electro-anatomical approaches, the impedance method therein disclosed enables safe and effective arrhythmia treatment.

4 Claims, 5 Drawing Sheets

U.S. PATENT DOCUMENTS

| | | |
|---|---|---|
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,537,570 B2 * | 5/2009 | Kastelein ................ 600/508 |
| 7,630,752 B2 * | 12/2009 | Viswanathan ........... 600/409 |
| 7,715,907 B2 * | 5/2010 | Koertge et al. ........... 600/515 |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0028183 A1 * | 2/2003 | Sanchez et al. ............ 606/34 |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 * | 3/2007 | Pappone ................... 128/898 |
| 2007/0073288 A1 | 3/2007 | Hall et al. |
| 2007/0088197 A1 | 4/2007 | Garibaldi et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |
| 2008/0300588 A1 * | 12/2008 | Groth et al. ............... 606/34 |
| 2009/0248014 A1 * | 10/2009 | Shachar et al. ............ 606/41 |

* cited by examiner

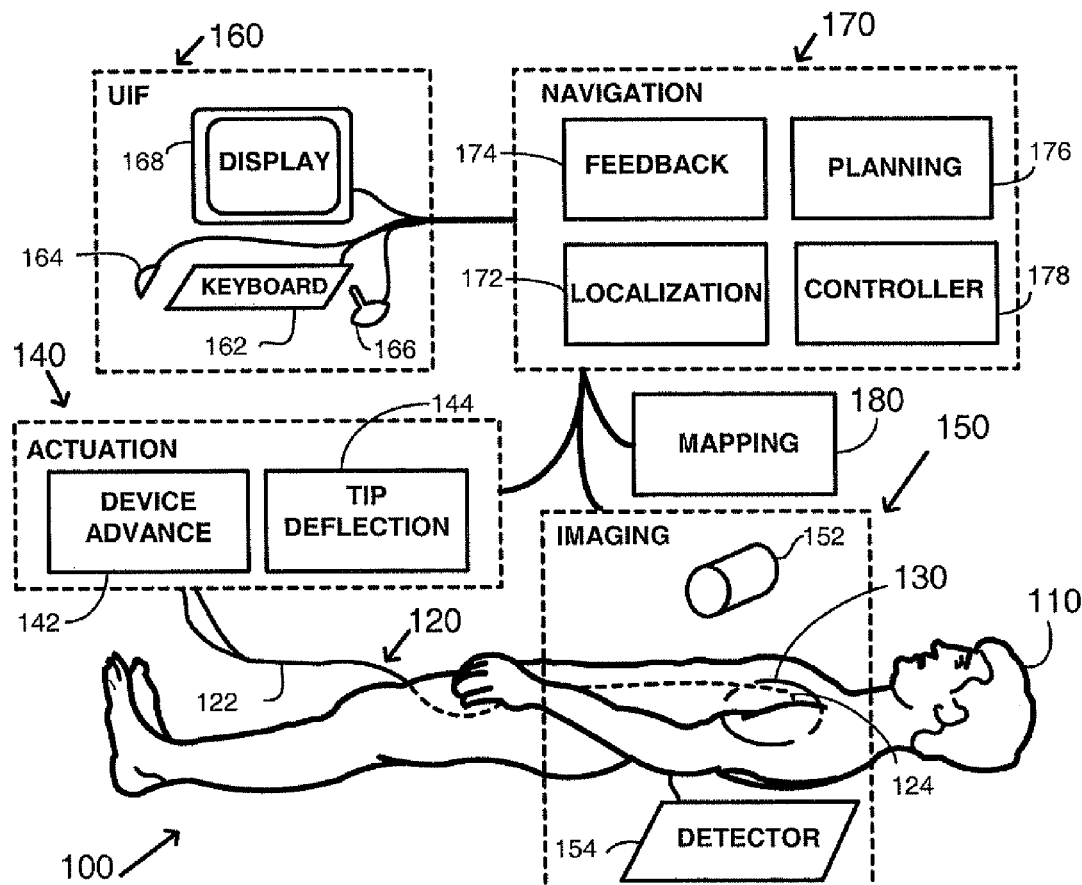
Fig. 1-A
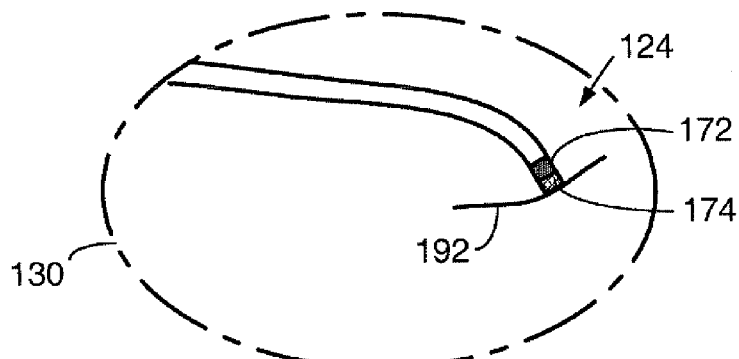
Fig. 1-B

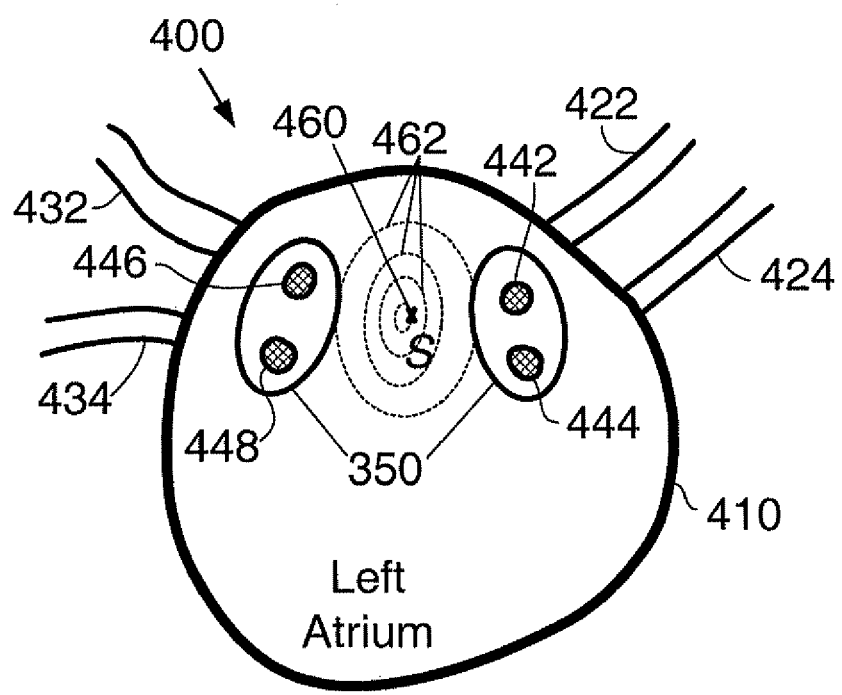
FIG. 4-A
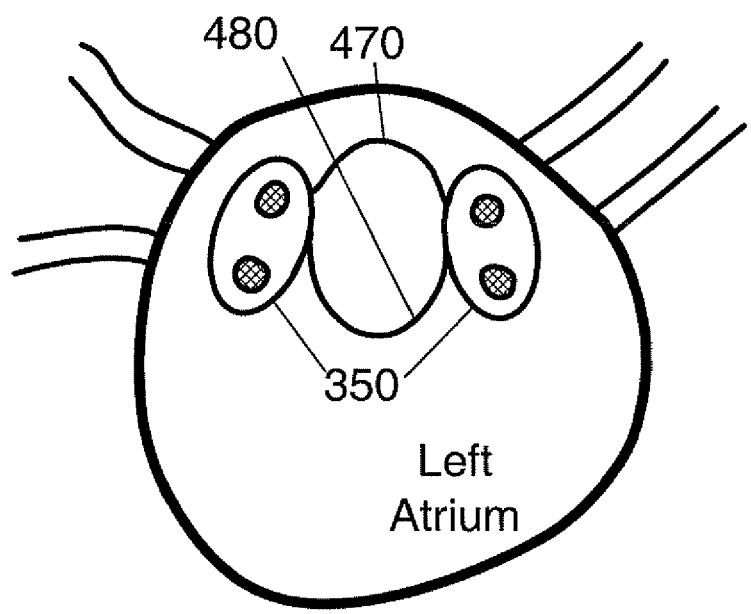
FIG. 4-B

IMPEDANCE-BASED CARDIAC THERAPY PLANNING METHOD WITH A REMOTE SURGICAL NAVIGATION SYSTEM

CROSS-REFERENCE TO RELATED APPLICATIONS

This application claims the benefit of U.S. Provisional Patent Application Ser. No. 60/843,529, filed Sep. 8, 2006, the entire disclosure of which is incorporated herein by reference.

FIELD OF THE INVENTION

This invention relates to the planning of intra-cardiac chamber ablation therapy for the treatment of arrhythmias, fibrillation, flutter, and other disorders of the cardiac rhythm with a remote surgical navigation system.

BACKGROUND

Interventional medicine is the collection of medical procedures in which access to the site of treatment is made by navigation through one of the subject's blood vessels, body cavities or lumens. Interventional medicine technologies have been applied to the manipulation of medical instruments such as guide wires and catheters which contact tissues during surgical navigation procedures, making these procedures more precise, repeatable, and less dependent on the device manipulation skills of the physician. Remote navigation of medical devices is a recent technology that has the potential to provide major improvements to minimally invasive medical procedures. Several presently available interventional medical systems for directing the distal end of a medical device use computer-assisted navigation and a display means for providing an image of the medical device within the anatomy. Such systems can display a projection or image of the medical device being navigated to a target location obtained from an imaging system such as x-ray fluoroscopy or computed tomography; the surgical navigation being effected through means such as remote control of the orientation of the device distal end and proximal advancement of the medical device.

Right-heart catheterization enables pressure and oxygen saturation measure in the right heart chambers, and helps in the diagnosis of tricuspid valve abnormalities. Left-heart catheterization enables evaluation of mitral and aortic valvular defects and myocardial disease. In a typical minimally invasive intervention, data are collected from a catheter or other interventional device that are of great use in treatment planning, guidance, monitoring, and control. In electrophysiology applications, for example, electrical signal measurements are taken at a number of points within the cardiac cavities to map cardiac activity and determine the source of arrhythmias.

The heart beat is regulated by the cardiac pacemaker located in the sinoatrial node; it generates electrical impulses at a typical rate of about 70 per minute. The impulses from the sinoatrial node propagate in a defined sequence to the other structures of the heart, resulting in atrial chambers contractions followed, after a delay of about 0.3 s, by ventricles contractions. Many types of heart disease induce cardiac rhythm disturbances, such as heart-attack-induced ventricular dysrhythmia. Arrhythmias and dysrhythmias disrupt the pumping action of the heart and can lead to cardiac arrest.

There exist a number of mechanisms that disturb the heart rhythm. Arrhythmias can originate from an ectopic focus or center, that may be located at any point within the heart, essentially an abnormally placed secondary pacemaker driving the heart at a higher rate than normal. Disturbances in the cardiac rhythm also originate from the formation of a disorganized electrical circuit, called "re-entry" and resulting in a reentrant rhythm, usually located within the atrium, at the junction between an atrium and a ventricle, or within a ventricle. In a reentrant rhythm, an impulse circulates continuously in a local, damaged area of the heart, causing irregular heart stimulation at an abnormally high rate. Finally various forms of heart block can develop, preventing the normal propagation of the electrical impulses through the heart, slowing down or completely stopping the heart. Heart blocks originate in a point of local heart damage, and can be located within a chamber, or at the junction of two chambers. Examples of clinically classified arrhythmias include paroxysmal or chronic extra-systolic activity, either atrial (mostly benign) or ventricular; auricular flutter, an irregularity of the heartbeat in which contractions of the auricle exceed in number those of the ventricle, atrial fibrillation, an irregular and uncoordinated rhythm of contraction of the atrial muscles; and ventricular tachycardia or fibrillation (rapidly lethal), among other conditions.

Atrial fibrillation is the most common of the major heart rhythm irregularities, and occurs, for example, in spasms following chest surgery, after pulmonary vein embolism, or as a consequence of serious fever or infections. Defects or disease of the mitral valve, when severe enough, will also cause atrial fibrillation, particularly in case of congestive heart failure (when the heart is unable to pump adequate quantities of blood into the body's circulatory system). Continuous atrial fibrillation might lead to the formation of clots and related risks of embolism.

In recent years, the development of minimally invasive techniques has lead to the emergence of intra-cardiac radiofrequency (RF) ablation as a viable alternative of reduced morbidity to surgery for the treatment of most arrhythmias resistant to drug approaches or to treatment via pacemaker or defibrillator approaches. RF ablation aims at eliminating the damaged tissue at the site of ectopic activity centers, or at the elimination of reentrant circuit loops via tissue fulguration. Most ablation treatments rely on anatomical imaging techniques, electrical activity mapping, or a combination of electro-anatomical approaches. RF ablation proceeds by depositing energy to locally raise the tissue temperature to fulguration.

RF ablation is the treatment of choice for most atrial fibrillation cases. The right atrium is relatively easy to access via venous perforation, while left atrium access via an arterial retrograde approach is not practical with today's mechanical navigation systems, due to the number of turns required in accessing the atrium through two valves and the left ventricle. Current mechanical approaches instead access the left atrium through a venous approach to the right atrium, followed by trans-septal wall puncture (typically at the fossa ovalis) into the left atrium.

Circumferential pulmonary vein ablation (CPVA) is an effective treatment for left atrial fibrillation. The ability to understand and correctly reconstruct the left atrial and pulmonary vein anatomy is essential to deploy continuous effective ablation lines around the target regions at the pulmonary vein ostium—left atrial junctions. One of the potential advantages of CPVA over other techniques is the absence of pulmonary vein stenosis. However such an advantage is not always attained by use of ablation relying on an electro-anatomical approach.

SUMMARY

The present disclosure describes a method of identifying heart wall lines or contours for the performance of ablation therapy using a remote navigation system. The method relies on impedance measurements taken within a heart chamber, within a vein or artery, and in a transition zone at or near the vessel ostium. Such data are acquired and imported into the remote navigation system. In particular, the criteria for safe CPVA then become based on i) catheter anatomical position; ii) local electrogram characteristics, and iii) impedance measurements, thus significantly improving on the procedure safety and efficacy. Lines of equi-impedance are defined on the atrial wall near the ostium junction, that isolate each of the pulmonary veins in turn; as the impedance value is decreased, the two (both left or right) pulmonary vein contours increase in perimeter till they join at a contact point; the resulting contour line is retained as the ablation line around the two (left or right) pulmonary vein ostia.

Further, the disclosure describes a method of defining ablation lines joining the above-defined left and right CPVA ablation lines, or any set of pre-defined ablation lines, Lines of iso-impedance are followed from one of the ostia (left or right) ablation lines to the other, typically lying on the posterior atrium wall surface.

Once the ablation lines or contours are defined on the remote navigation system, they become targets for navigating the catheter or other ablation device using the remote navigation system in order to deliver ablation therapy.

BRIEF DESCRIPTION OF THE DRAWINGS

FIG. 1-A is a schematic view of a subject positioned in a projection imaging system for an interventional procedure such as electrophysiology diagnosis and therapy using a controlled minimally invasive modality;

FIG. 1-B is an enlarged perspective view of an interventional device with the distal end being in tissue contact within a theater of intervention;

FIG. 4-A is a front elevation view showing schematically the selection of additional atrial ablation lines connecting the left and right pulmonary veins ablation lines;

FIG. 4-B is a front elevation view showing the CPVA ablation lines obtained by the process illustrated in FIG. 4-A.

Corresponding reference numerals indicate corresponding points throughout the several views of the drawings.

DETAILED DESCRIPTION OF THE INVENTION

Figure 2:
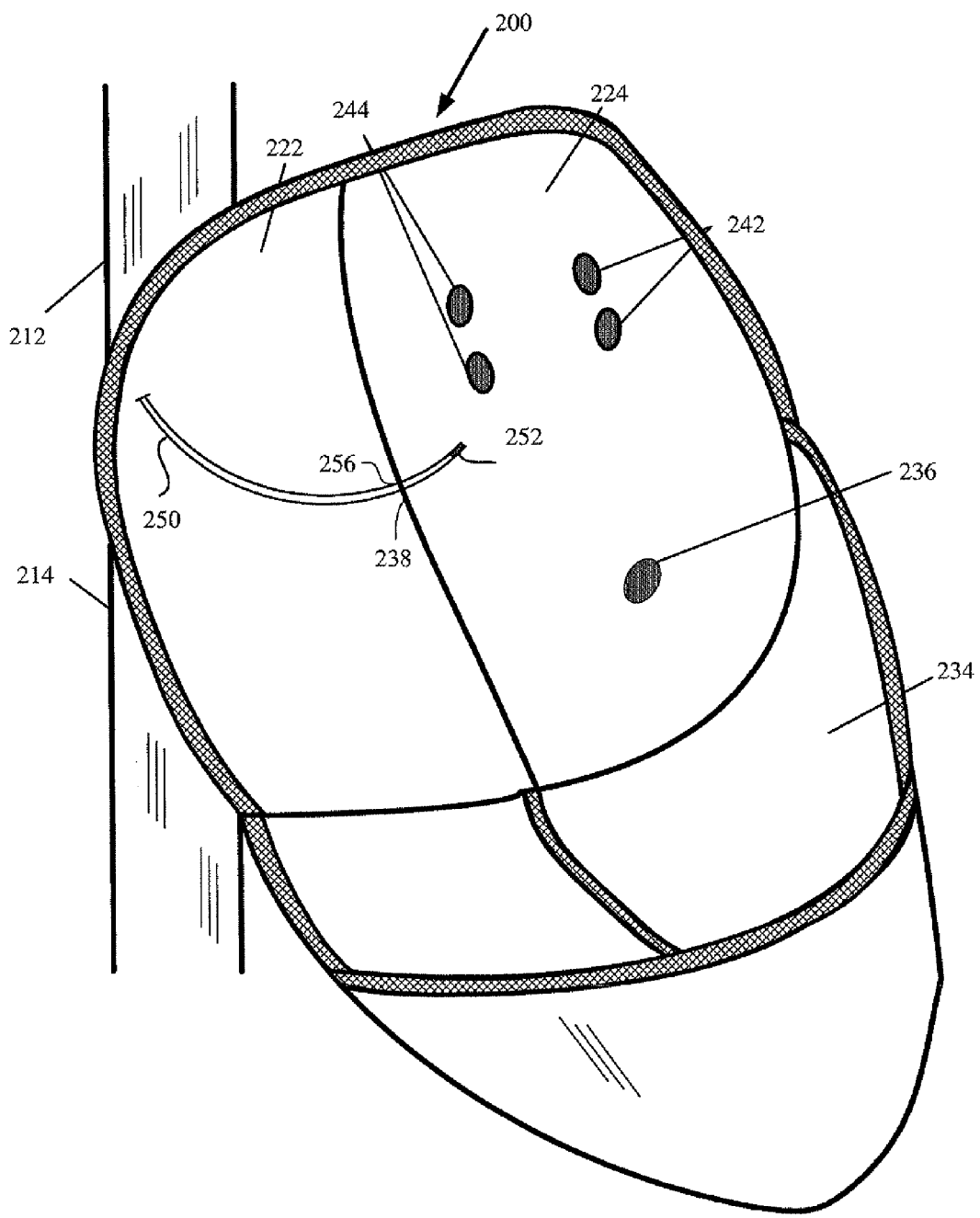
FIG. 2 is a front perspective sectional view of a heart showing typical trans-septal approach to left atrial ablation therapy.

As illustrated in FIG. 1, a subject 110 is positioned within an interventional system, 100. An elongate navigable medical device 120 having a proximal end 122 and a distal end 124 is provided for use in the interventional system 100, FIG. 1-A, and the medical device is inserted into a blood vessel of the subject and navigated to an intervention volume 130. A means of applying force and orienting the device distal end 124 is provided, as illustrated by actuation block 140 comprising a device advance/retraction component 142 and a tip deflection component 144. The tip deflection means may be one of (i) a mechanical pull-wire system; (ii) a hydraulic or pneumatic system; (iii) an electrostrictive system; (iv) a magnetic system; or (v) other navigation system for remotely orienting the distal tip. For illustration, in magnetic navigation a magnetic field externally generated by a magnet(s) assembly (not shown) orients a small magnetically responsive element located at the device distal end (172, FIG. 1-B). Real time information is provided to the physician, for example by an x-ray imaging chain 150 comprising an x-ray tube 152 and an x-ray detector 154, and also possibly by use of a three-dimensional device localization system such as a set of electromagnetic wave receivers located at the device distal end (not shown) and associated external electromagnetic wave emitters (not shown), or other localization device with similar effect. The physician provides inputs to the navigation system through a User-Interface sub-system 160 comprising user interfaces devices such as a display 168, a keyboard 162, mouse 164, joystick 166, and similar input devices. Display 168 also shows real-time image information acquired by the imaging system 150 and the three-dimensional localization system. UIF system 160 relays inputs from the user to a navigation system 170 comprising a localization block 172, a feedback block 174, a planning block 176, and a controller 178. Navigation sequences are determined by the planning block 176 based on inputs from the user, pre-operative data, localization data processed by localization block 172 and real-time imaging and feedback data processed by feedback block 174; the navigation sequence instructions are then sent to the controller 178 that actuates the device through actuation block 140 to effect device advance and tip deflection. Other navigation sensors might include an ultrasound device or other device appropriate for the determination of distance from the device tip to the tissue (not shown). Further device tip feedback data include relative tip and tissues positions information provided by an imaging system, predictive device modeling, or device localization system. In closed loop implementation, the navigation system 170 automatically provides input commands to the device advance and tip orientation actuation components based on feedback data and previously provided input instructions; in semi-closed loop implementations, the physician fine-tunes the navigation control, based in part upon displayed and other feedback data. Control commands and feedback data may be communicated from the user interface and navigation system 170 to the device and from the device back to system 170 (feedback), through cables or other means, such as wireless communications and interfaces. System 100 preferably comprises an electromechanical device advancer 142, capable of precise device advance and retraction based on corresponding control commands. In electrophysiology applications, a mapping component 180 collects electrical activity data measured at the device tip 124 by electrode 174 in contact with tissue 192, FIG. 1-B, at locations identified by the localization system described above. Based on mapping information, and associated three-dimensional (3D) model, the navigation system 170 identifies ablation lines as described below. The device may also comprise a tip RF component for tissue fulguration and ablation during therapy (RF component not shown).

Once target locations such as ablation points or contours are identified, either a closed loop or a semi-closed loop implementation can be used to drive or steer the medical device with the remote navigation system to the desired target location or successively to a sequence of locations. While one preferred embodiment of such a remote navigation system is a magnetic navigation system, for example the Niobe® system manufactured by Stereotaxis, Inc., St. Louis, Mo., other preferred embodiments could be based on mechanical, electrostrictive, hydraulic, magnetostrictive, or other actuation technologies known to those skilled in the art. Thus the type of remote navigation system that is used is not limited to any description herein, the scope of the invention being limited only by the attached claims.

Referring now to FIG. 2, retrograde left atrium arterial access would necessitate navigation through the aorta, aortic valve, left ventricle 234, and mitral valve, and is usually not practical using mechanical navigation systems, due to the loss of torque and force transmission to the catheter distal end resulting in loss of maneuverability after a few navigation turns. Accordingly, as schematically illustrated in FIG. 2, access to the left atrium 224 typically requires venous navigation of the interventional device 250 through either the superior 212 or inferior 214 vena cava to the right atrium 222, followed by a trans-septal puncture 256, typically through the fossa ovalis 238, an area of reduced septum wall thickness and of specific structure, normally completely closed only during the later stages of an embryo's formation or in early infanthood. Various methods may be used to plan and guide the navigation of an interventional device to a specific heart location such as the left 242 or right 244 inferior and superior pulmonary veins. X-ray fluoroscopy imaging may be used to provide real-time imaging. Registration of such imaging to a pre-operative three-dimensional (3D) CT image data set facilitates orientation in a complex volumetric anatomy. Ultrasound may be employed, although intra-cardiac ultrasound requires the navigation of a probe to or near the chamber of interest (and this requires a second trans-septal puncture for left atrium access). Localization methods and apparatus relying on electromagnetic waves (in the kilo-hertz frequency range) have been developed whereby signals of known frequencies and amplitudes are generated external to the subject and detected by a set of three receiver coils located at the catheter tip. Such methods are disclosed in U.S. Pat. No. 7,020,512, entitled Method of Localizing Medical Devices, which is incorporated by reference. These tools enable precise localization of the catheter tip within a 3D frame of reference, and therefore allow 3D cardiac mapping. In one implementation, these tools enable 3D mapping of parameters such as electrogram activity collected at a series of known heart locations. Accordingly, both anatomical methods, based on local tissue features, and physiological methods, based on the measurements of quantities of direct interest such as electric signals, are available to plan and guide ablation interventions. Three-dimensional electro-anatomical mapping typically distinguishes with high accuracy between reentrant and focal cardiac rhythm disturbance sites. Electrical impedance, as measured between an electrode located at the distal end of a catheter and a second electrode for example affixed to the subject's back, is useful in characterizing measurement locations as being within the atrium (lower impedance), deep within a pulmonary vein (higher impedance), or in a transition zone near the vein ostium. Measured impedance variations represent local heart chamber and pulmonary vein chamber impedance changes. Such impedance measurements can be used by themselves or in conjunction with electro-anatomical mapping to obtain improved tissue characterization and labeling. In practice, impedance measurements are taken at a number of atrial points. The catheter tip 252 is then preferably inserted deep into a pulmonary vein 242, 244, to define a pulmonary vein impedance level; the catheter is then withdrawn slowly to the atrium, and a series of impedance measurements are taken in the transition zone near the vessel ostium. Typically, the vein impedance will be distinguishingly higher as compared to the average atrium impedance. This method of measurement allows the definition of an impedance threshold, such that all points below the threshold are known to be within the atrium, while points at the threshold value are within the atrium and near the ostium transition zone.

Figure 3:
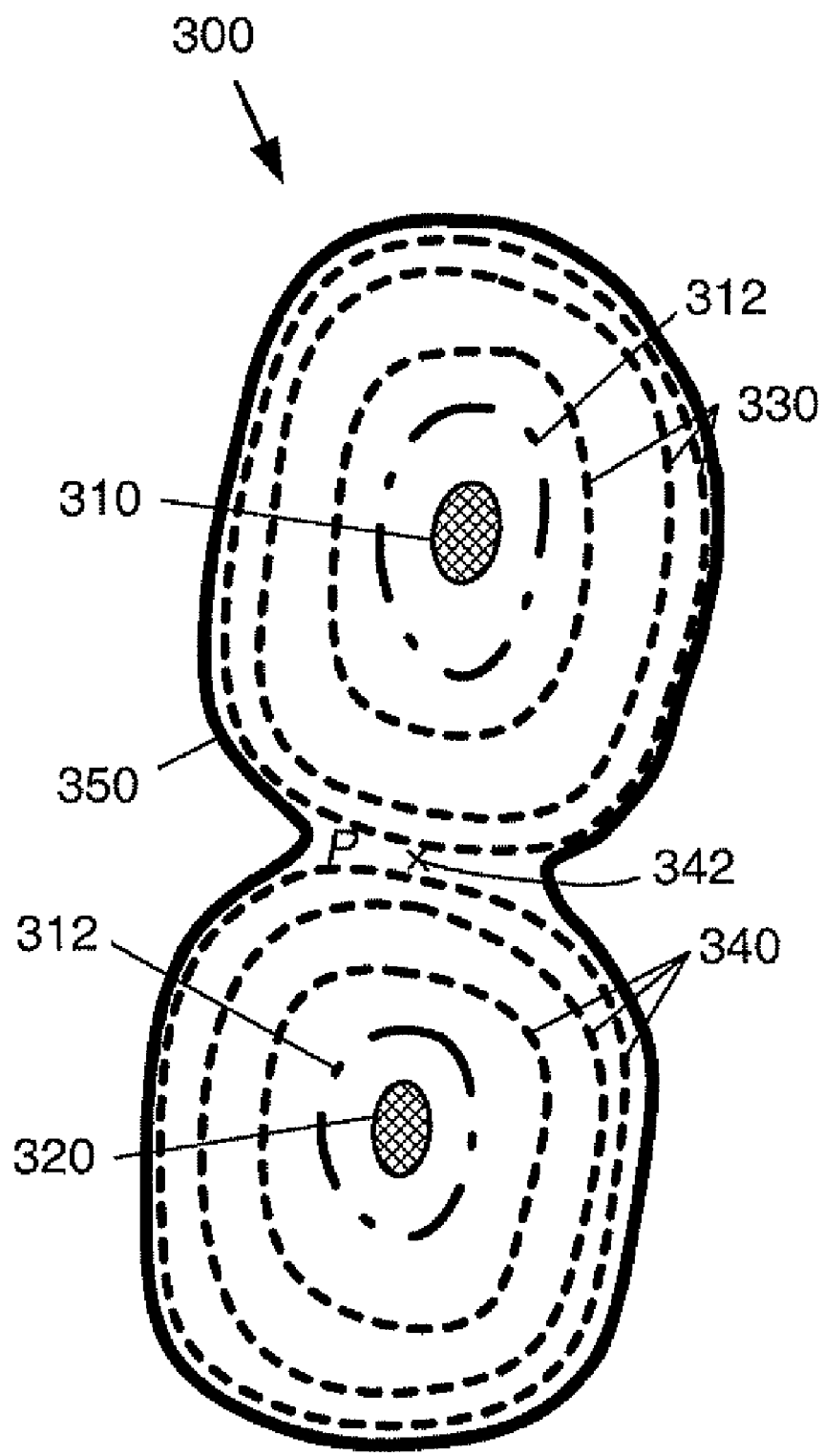
FIG. 3 is a front elevation view of a portion of a heart wall illustrating a method of selecting a line of ablation around a pair of pulmonary veins.

Accordingly a method of defining ablation lines as shown in FIG. 3 is disclosed as follows. Given atrial and superior pulmonary vein impedance measurements, define an impedance threshold $Z_T$ as described above; next, and starting with a contour impedance value $Z_C$ set at the impedance threshold $Z_C = Z_T$, follow a line of iso-impedance 312 within the atrium; such a line will naturally loop around the vein ostium 310. Lines of iso-impedance can be defined from the available electrical activity and impedance mapping data, by use of a 3D model defined from the measurements by interpolation and/or triangulation. The procedure is repeated with the inferior pulmonary vein 320 on the same side of the atrium, thereby defining a second iso-impedance contour 312 around the second vein 320. Two situations can then arise: (1) should the iso-impedance contours intersect, the respective contours impedance threshold values are increased by a predetermined amount dependent upon the selected threshold and the impedance value range between atrium and pulmonary vein, and the procedure repeated; selection of a higher impedance value ensures that the circumventing contours will constrict toward the ostia; the steps above are repeated till the two iso-impedance contours are essentially tangent on at least one point P 342, as illustrated in FIG. 3; the contour formed by following both tangent contours around the two pulmonary veins defines a single contour (not shown); now decreasing the impedance by a predetermined amount defines a final contour 350 that defines a single area (in the sense that any two points within the enclosed area may be joined by a line that does not intersect the contour); (2) should the two original pulmonary vein contours do not intersect, the respective contours impedance threshold values are decreased incrementally, new corresponding contours 330, 340 defined, till the two contours are tangent on at least one point P 342; the union of the two tangent contours then defines a single contour as in step (1), and an additional impedance threshold value decrement is applied to define the final, ablation contour 350.

A given point P on the atrium surface may be determined to belong to the interior of an iso-impedance $Z = Z_C$ pulmonary vein circumferential contour C in the following manner. A least-distance path is traced from the contour C center of gravity $G_C$ to the point P; should the impedance of a point M on the line $G_C P$ always remain greater than the contour defining impedance $Z_C$, then P belongs to the interior of contour C. Similarly, given a threshold value $\epsilon > 0$, two contours $C_1$ and $C_2$ may be said to be tangent with respect to $\epsilon$ or intersecting if:

$$\text{Min} \|P_1 - P_2\| < \epsilon, P_1 \epsilon C_1, P_2 \epsilon C_2.$$

The determination of tangency versus intersection may be achieved by considering a subset of points $P_1$, $P_2$ such that:

$$\|P_1 - P_2\| < \epsilon, P_1 \epsilon C_1, P_2 \epsilon C_2.$$

and determining whether any points in that subset belongs to both $C_1$ and $C_2$. Many other techniques in the fields of numerical analysis and computer graphics are available to determine whether two contours on the same surface intersect, are tangent (with respect to threshold value $\epsilon$), or neither, as is known in the art. In practice, the threshold value $\epsilon$ is set as a function of the predefined impedance increments.

Referring now to FIG. 4-A, once the two contours encircling the left 422, 424 and right 432, 434 pulmonary vein pair ostia have been defined, as described above, it is often useful for successful arrhythmia treatment to further ablate tissues along joining lines on the atrial wall. FIG. 4-A shows a method of selecting ablation lines joining two previously identified atrial circumferential ablation lines 350 surrounding respectively the left 442, 444 and right 446, 448 pulmonary veins ostia. The lines joining the two pulmonary vein contours are defined as follows. A seed point S 460 is selected on the atrial wall, approximately midway on the surface linking the pulmonary vein contours. As both pairs of pulmonary vein ostia are typically located on the atrium posterior wall 410, the seed point is selected as a local impedance minimum within the area that encompasses both sets of ostia. Associated iso-impedance contours of increasing impedance value are then defined, 462. As the impedance within the atrium is known to be lower than the threshold impedance value retained to define the circumferential pulmonary vein contours, the first iso-impedance contour thus defined will not intersect contours 350. The selected impedance value is then increased by a predetermined amount till intersection occurs. Should one of the two contour-selecting threshold values associated with the pulmonary vein ablation contours 350 be higher than the other, the impedance value is increased incrementally till the second pulmonary vein contour is also intersected. The corresponding lines 470, 480, then define two joining ablation lines, typically located on the posterior atrium wall, as illustrated in FIG. 4-B.

Figure 5:
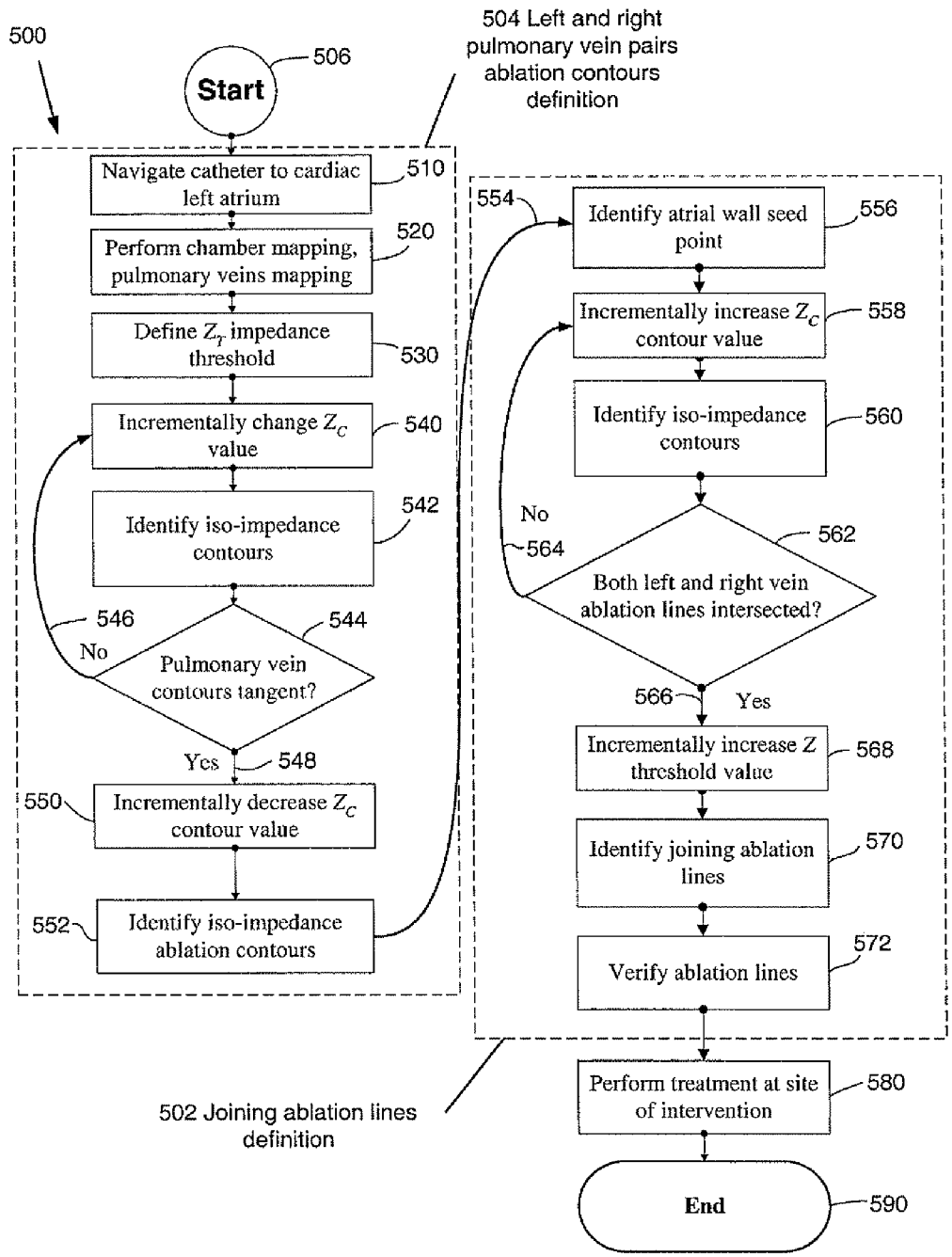
FIG. 5 is a workflow chart for a method of treatment planning according to the present invention.

Accordingly, a method is disclosed that enables definition of impedance-based ablation lines definition and subsequent treatment of specific conditions. FIG. 5 provides a flowchart for an exemplary embodiment of the method. In the application illustrated, the objective of the intervention is the treatment of a left atrial fibrillation. A catheter or interventional device suitable for RF ablation is navigated to the left atrium, 510. Chamber electrical activity and impedance mapping is performed, 520, as well as pulmonary veins mapping. The mapping comprises acquiring a multiplicity of measurements at known locations within the heart structures, sufficient for the generation of a 3D model of impedance and activity. For a given pulmonary vein, an impedance threshold $Z_T$ is then defined 530 by comparing the average atrium impedance value $Z_A$ to the average pulmonary impedance value $Z_V$. The contour impedance value $Z_C$ is initially set at the threshold value $Z_T$, 540, and iso-impedance contours are derived from the 3D model, 542. The procedure is repeated for the other vein in the vein pair (not shown). Then the two respective vein iso-impedance contours are analyzed, and a determination is made as to whether the contours are tangent, 544. Determination of intersection and tangency are made by use of graphics analysis techniques, as known in the art. If the contours are not tangent, 546, the contour impedance value $Z_C$ is increased or decreased by a predetermined amount depending on whether the contours intersect or not. The procedure is then iterated till the contours are tangent, 548. The contour impedance value $Z_C$ is then decreased by a predetermined amount to define a single contour encompassing a single heart area, 550. The resulting contour is retained as the vein pair ablation contour, 552. The procedure is repeated for the second vein pair (not shown), and junction lines are defined 554 as follows.

A posterior (in normal anatomy) atrial wall seed point is identified by retaining the point with minimum impedance value within an area encompassing the two previously defined vein ablation contours, 556. Then a contour impedance value $Z_C$, initially set to the seed point impedance value, is increased by a predetermined amount, 558. Iso-impedance contours for $Z_C$ are identified from the 3D mapping data and model, 560. It is then determined whether the newly defined iso-impedance contour intersects both of the previously defined vein ablation contours, 562. If not, branch 564, the method is iterated till a higher impedance contour value leads the newly defined iso-impedance contour to intersect both vein ablation contours, 566. The resulting impedance value is then increased by a predetermined amount, 568, and joining ablation lines are identified that connect the left and right pulmonary vein ablation contours, 570. Finally, the set of ablation lines identified as a result of this algorithm are verified for positioning, distance to the ostia, and electrical activity by the intervening physician, 572, treatment occurs, 580 and the method terminates, 590.

Prior methods of reducing the incidence of pulmonary vein stenosis include the use of intra-cardiac ultrasound. However, this invasive technique requires and additional trans-septal perforation for left atrium ablation treatment. Impedance mapping by itself or in combination with electro-anatomical mapping leads to the identification of suitable sites for ablation with high sensitivity and specificity, and positive predictive value. When used with a 3D map, impedance based mapping can become an extremely valuable surrogate marker for the presence of transitional or venous tissue at the catheter location. Impedance information can be readily obtained at no additional risk or cost, and can be readily applied to guide ablation. The methods according to the principles of the present invention enable automatic impedance-based contour identification for RF ablation, and improve upon ablation contour identification by anatomical or electrical mapping only.

The advantages of the above described embodiment and improvements should be readily apparent to one skilled in the art, as to enabling the planning of cardiac ablation therapy. Additional design considerations may be incorporated without departing from the spirit and scope of the invention. Accordingly, it is not intended that the invention be limited by the particular embodiment or form described above, but by the appended claims.

What I claim is:

1. A method of defining ablation lines in the left atrium of the heart, comprising:
   i) performing impedance mapping of the left atrium and a pair of pulmonary veins;
   ii) for each pulmonary vein, defining an impedance threshold value corresponding to the pulmonary vein ostium;
   iii) defining iso-impedance contours for each of the veins based on corresponding impedance threshold ii) and impedance mapping i);
   iv) determining whether the two iso-impedance contours iii) are a) crossing; b) tangent; or c) neither;
   v) increasing or decreasing the two respective impedance contour values by a predetermined amount if the contours are crossing, or not, respectively, and defining corresponding iso-impedance contours;
   vi) iterating over steps iv) and v) until the two contours are tangent, and defining an associated single iso-impedance contour; and
   vii) retaining the corresponding iso-impedance contour as a pulmonary vein pair ablation line.

2. The method of claim 1, further comprising decreasing the contour impedance of the single contour of step vi) by a second predetermined amount and retaining the corresponding iso-impedance contour as a pulmonary vein pair ablation line.

3. The method of claim 1, further comprising using imaging to guide the selection of the ablation lines.

4. The method of claim 1, further comprising performing a plurality of electrical activity measurements within the left atrium to guide the selection of the ablation lines.

* * * * *